(12) United States Patent
Gräfe et al.

(10) Patent No.: US 8,263,557 B2
(45) Date of Patent: Sep. 11, 2012

(54) METHOD AND MIXTURE FOR IN VIVO PHOTOCHEMICAL CROSS-LINKING OF COLLAGEN

(75) Inventors: Susanna Gräfe, Jena (DE); Wolfgang Neuberger, Labuan (MY); Danilo Castro, Montevideo (UY)

(73) Assignee: Biolitec Pharma Marketing Ltd, F.T. Labuan (MY)

( * ) Notice: Subject to any disclaimer, the term of this patent is extended or adjusted under 35 U.S.C. 154(b) by 684 days.

(21) Appl. No.: 12/227,079

(22) PCT Filed: Jul. 27, 2007

(86) PCT No.: PCT/US2007/016952
§ 371 (c)(1),
(2), (4) Date: Nov. 6, 2008

(87) PCT Pub. No.: WO2008/013962
PCT Pub. Date: Jan. 31, 2008

(65) Prior Publication Data
US 2009/0171262 A1    Jul. 2, 2009

Related U.S. Application Data

(60) Provisional application No. 60/834,059, filed on Jul. 28, 2006.

(51) Int. Cl.
*A61K 38/17* (2006.01)
*C07D 487/22* (2006.01)
*A61N 5/06* (2006.01)

(52) U.S. Cl. ...... 514/16.5; 514/17.1; 514/801; 540/145; 604/20

(58) Field of Classification Search ............. 514/16.5, 514/17.1, 801; 540/145; 604/20
See application file for complete search history.

(56) References Cited

U.S. PATENT DOCUMENTS

| 5,807,881 A * | 9/1998 | Leong et al. ............ 514/410 |
| 5,913,884 A * | 6/1999 | Trauner et al. .......... 607/88 |
| 7,691,829 B2 * | 4/2010 | Petito et al. ............. 514/54 |

* cited by examiner

*Primary Examiner* — Rosanne Kosson
(74) *Attorney, Agent, or Firm* — BJ Associates; Bolesh J. Skutnik

(57) ABSTRACT

A method and a composition for photochemical cross linking of collagen by photoactive agent in-vivo are presented. The method includes a non-toxic photoactive formulation of the composition with collagen, which is administered to treatment area locally; followed by irradiation with suitable wavelength. In one of the embodiment liposomal formulated mTHPC is added to the collagen and is irradiated with a 652 nm laser, resulting in producing efficient collagen scaffolds with strengthen and stabilized microstructure, thus improving the physiochemical properties of the collagen scaffold. It improves the thermostability, mechanical property and swelling ratio of newly formed scaffold. Photochemical cross-linked collagens shows antimicrobial effect, when irradiated with suitable wavelength it disinfects the treatment site and curbs microbial growth.

3 Claims, 5 Drawing Sheets

Before PDT Foslip Treatment     After 3 days PDT Foslip Treatment though, more specifically it relates to a
METHOD AND MIXTURE FOR IN VIVO PHOTOCHEMICAL CROSS-LINKING OF COLLAGEN Domestic Priority under 35 USC 119(e). This application claims the benefit of U.S. Provisional Application Ser. No. 60/834,059, filed Jul. 28, 2006, which is incorporated by reference herein.

BACKGROUND OF THE INVENTION

1. Field of the invention

Present invention relates to structural proteins like collagen repairs in general, while, more specifically it relates to a method of photochemical cross linking of collagen fibrils using photoactive agent, whereby it could be used in different types of tissue repair and regeneration in human and animals.

2. Invention Disclosure Statement

The protein: collagen is the main substance of connective tissue and is present in humans. In mammals collagen is the most abundant protein. Collagen gives many different organs and tissues support and elastic properties. It has been found in many different tissues and organs like bones, tendons, (hyaline) cartilage, blood vessels, teeth, cornea, skin, etc. It prevents organs/tissues to tear or loose their functional shape when they are exposed to sudden and wild movements.

Collagens are fibrous protein composed on amino acids. The most abundant amino acids are glycine, proline and hydroxyproline. General collagen structure consists of three polypeptides, each of which is a left-handed helix, intertwined into a right-handed triple helix. Human body is mainly composed of collagen type I.II.III, however many other types are also present.

Collagen is a natural biomaterial commonly used in tissue engineering and repair; it has negligible immune rejection and excellent biocompatibility. But unprocessed collagen is mechanically weak and vulnerable to chemical and enzymatic attacks that limits its use.

Collagen can be cross-linked to increase its molecular stability and mechanical properties. The most basic mode of action is the covalent intermolecular cross-link formation between collagen fibrils. Cross-linking improves strengths, resorption rate and biocompatiblilty of the scaffold.

The collagen can be strengthen and stabilized, either by chemical or physical methods of cross-linking. In Chemical method, some chemical cross-linking agents include: glutaraldehyde, formaldehyde, 1-ethyl-3(3-dimethylaminoproplyl)-carbodimide (EDC) etc are used for cross-linking to improve the Physico-chemical properties of collagen; however, this method is limited because of induction of cytotoxicity and calcification and stiffness in host tissue due to incomplete removal of the toxic residues, aldehydes, and other metabolites. Physical methods of cross-linking can be achieved by heat, dehydrothermal treatment (DHT), and UV- and γ-irradiation. These methods compromise the stability of collagen due to thermal degradation and collagen denaturation is bound to occur due to heat. These cross-linking processes are very time comsuming, usually requiring hours or days to completer and cause significant degradation to the collagen molecules.

Photochemical method provides and alternative method for cross-linking collagen in the presence of light and photosensitizing agents. In U.S. Pat. 6,783,539 by Timberlake et al., discloses uses of phototriggerable tethered diazopyruvate composition and method for crossing linking of proteins using the same. A wavelength range of 330-400 nm is used for activation of photoactive compound and cross-linking of the protein. The wavelength range used here minimal penetration and is useful only for certain medical application. Cross-linking is done prior to application in vivo.

A better method of collagen cross linking needs to be developed which would in turn improve the physio-chemical properties of collagen such as water-binding capacity, mechanical properties and thermostability thus enhancing better tissue healing without scaring or damaging the collagen. The present invention aims to provide this.

Objectives And Brief Summary Of The Invention

It is an objective of the present invention to provide a photochemical method for cross-linking of collagen in vivo.

It is another objective of the present invention to provide a non-toxic photoactive formulation with collagen.

It is still another objective of the present invention to use such photochemical cross linking method for tissue engineering and repair.

It is also another objective of the present invention to use a suitable wavelength matching the absorption spectrum of photoactive compound.

It is further objective of the present invention to use the photochemical cross-linked collagen in wound closures and cosmetic applications.

It is yet another objective of the present invention to provide a non-toxic, highly stable collagen scaffold, having optimal pore size.

Briefly stated present invention provides a method and compositions for photochemical cross linking of collagen by photoactive agent in-vivo. The method includes a non-toxic photoactive formulation of the composition with collagen, which is administered to treatment area locally followed by irradiation with suitable wavelength. In one of the embodiment liposomal formulated mTHPC is added to the collagen and is irradiated with a 652 nm laser, resulting in producing efficient collagen scaffolds with strengthened and stabilized microstructure, thus improving the physiochemical properties of the collagen scaffold. It improves the thermostability, mechanical property and swelling ratio of newly formed scaffold. Photochemical cross-linking of collagen in vivo also shows an antimicrobial effect. When irradiated with a suitable wavelength, it disinfects the treatment site and curbs microbial growth.

The above and other objects, features and advantages of the present invention will become apparent from the following description read in conjunction with the accompanying drawings.

DETAILED DESCRIPTION OF PREFERRED EMBODIMENTS

Figure 1:
FIG. 1—depicts the non-irradiated collagen picture with mTHPC.

Collagen is a natural biomaterial used for tissue reconstruction in third degree burns, wounds and for cosmetic application. Collagen as currently available has several drawbacks like being mechanically weak, low stability, swelling rapidly in water and being susceptible to chemical and enzymatic attack when implanted.

Physiochemical properties of collagen fibers are somewhat improved by physical or chemical method of cross-linking. Collagens cross-linked by chemical methods, however, have a risk of potential toxicity of residual molecules or compounds after implantation. While in the physical method, there is risk of denaturation of protein.

Photochemical cross-linking provides an alternative method to chemical and physical method of cross-linking collagen. Photochemical reactions of collagen in presence of light and photosensitizing agent causing cross-linking of collagen gives better physiochemical properties and also a non-cytotoxic collagen scaffold.

Photochemical cross-linked collagen has fine microstructure with interconnected nano-sized fibers forming micron-sized pores. The pore size is important in scaffold as they will determine cell adhesion and migration of the scaffold and as a result the success of healing. Photochemical cross-linking is able to stabilize the bonding forces between molecules and fibers so that the strengthened microstructure can survive a freeze-drying process. It also stabilizes the collagen scaffold thermally.

In the present invention a method for photochemical cross-linking of collagen using photoactive compound is disclosed. The method includes a non-toxic photoactive formulation for hydrophobic photosensitizer/precursor of photosensitizer with collagen, wherein preferably the hydrophobic photosensitizer is formulated into liposomes. The photoactive formulation is administered to the tissue either as injectable solution, sponge or wound dressing; this is followed by a short drug-light-interval (DLI) and, then, by irradiation with wavelength which activates selected photosensitizer. The photochemical reaction and the release of singlet oxygen causes a) disinfection of the treated area, and b) photochemical cross-linking of collagen by PDT leading to improved tissue engineering or tissue repair.

In a preferred embodiment collagen is used in combination with liposomal formulated temoporfin (chemical name: m-tetrahydroxyphenylchlorin, (mTHPC)) after a short DLI it is irradiated with a deeper penetrating 652 nm wavelength to produce efficient collagen scaffolds with strengthened and stabilized microstructures. It improves the physicochemical properties of the scaffolds, including the thermostability, mechanical properties and swelling ratio. The method used here in general is:
1. Collagen: equine or bovine collagen fibrils, 0.01 up to 5%, pH of the solution 6.0 to 8.0
2. mTHPC: photoactive dye, temoporfin, 5,10,15,20-tetra[m-hydroxyphenyl]chlorin
3. Liposomal Formulation of mTHPC, 1.5 mg/ml mTHPC, 6.0 mg/ml of dipalmitoylphosphatidylcholine (DPPC), 0.70 mg/ml of dipalmitoylphosphatidylglycerol (DPPG), 17.0 mg/ml of glucose and
4. Water.

All the above compounds are mixed to obtain the final photochemical composition. The final concentration of mTHPC will be approx. 0.05 mg/ml.

For cross-linking collagen matrix and disinfecting of treatment area, the formulation is irradiated with 652 nm. A laser (PDT laser Ceralas 652 nm, Biolitec AG) or lamp with appropriate wavelength could be used. Energy density of the light is about 10 to 20 $J/cm^2$ for in vivo cases. For production of collagen sponges ex vivo a higher density is commonly used, e.g. 100 $J/cm^2$. Generally a 10 to 100 $J/cm^2$ energy density can be used in the present invention.

The photochemical product, obtained of the above reaction, is better stabilized in structure with increased hydrothermal properties and resistance to enzymatic degradation.

Another embodiment of the present invention is use of fluorescence dye (mTHPC) in this formulation, and then the collagen fibril formation in the scaffold after irradiation with laser light can be controlled by break down of fluorescence of the dye. The light activated photosensitizing dye (mTHPC) is producing singlet oxygen to oxidize surrounding molecules (collagen cross-linking) and will bleach during this process.

The present invention is further illustrated by the following examples, but is not limited thereby.

EXAMPLE 1

Figure 2:
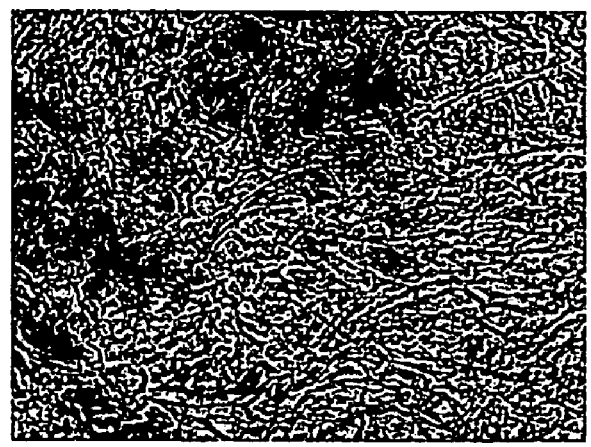
FIG. 2—show a picture of collagen with mTHPC after irradiation.

A collagen solution containing 1 mg/ml collagen A, at pH 1.0, was adjusted to pH 7.0 with 2.2% $NaCO_3$/0.8 M NaOH. The liposomal formulation of mTHPC was added to this. The final concentration of mTHPC in the formulation was 0.03 mg/ml. The formulation is irradiated with 652 nm laser (Ceralas, Biolitec AG) and 100 $J/cm^2$. The photochemical product have been investigates macroscopically and microscopically. Macroscopically the viscosity of the irradiated solution was higher than of the non-irradiated solution. Larger particles could be visible to the naked eye. Microscopically collagen fibrils in the irradiated solution are forming larger and more compact aggregates refer FIG. 2 than in the non-irradiated solution refer FIG. 1.

EXAMPLE 2

Animal Experiment
Animals: 18 Balb c Mice
Material:
    Gentacoll Sponge (Resorba GmbH),
    Kollagen Resorb Sponge (Resorba GmbH)
    Collagen Fibrils (Collagen Matrix Inc.)
    0.05 mg/ml Foslip Eighteen (18) Balb c mice were used for the study. Selected mice were narcotized and a small cut was inflicted in the neck region. Three treatment groups are set up: in the first treatment group a 5×5 mm piece of collagen saturated with liposomal formulation of mTHPC is implanted under the skin. After 30 min of incubation the area is irradiated with light at 652 nm at 10 $J/cm^2$ after which the region is covered with catgut and Hansaplast plaster spray.

In second group 50 µl liposomal formulation of mTHPC is injected subcutaneously and is incubated for 30 min followed by irradiating with light at 652 nm at 10 $J/cm^2$ followed by implanting non-treated collagen material under the skin opened by small cut. After which the region is covered and protected.

Third group is the control where in the mice wound is treated using collagen and laser irradiation with no liposomal formulation of mTHPC. Collagen products used in this treatment includes Gentacoll, Kollagen Resorb and collagen fibrils. In all the treatment groups 2 mice each is treated, for, each of these collagen products.

The treated mice were kept under observation to record the progress in wound healing. The progress in the wound healing process was recorded after 24 hours from treatment. It was noticed that all mice in treatment group 2 showed very good response with slight inflammation and wound was healed well; with all animals being vital in the group. while mice in treatment group 1 had shown strong redness and inflammation with hair loss in the treated area but the wound healing process was good by 12 days with hair growing back in the areas if treatment. Control group 3 showed very strong inflammatory action with redness and strong swelling in the initial period of treatment. All mice treated with collagen fibrils showed best biocompatibility compared to other collagen products used.

Figure 3:
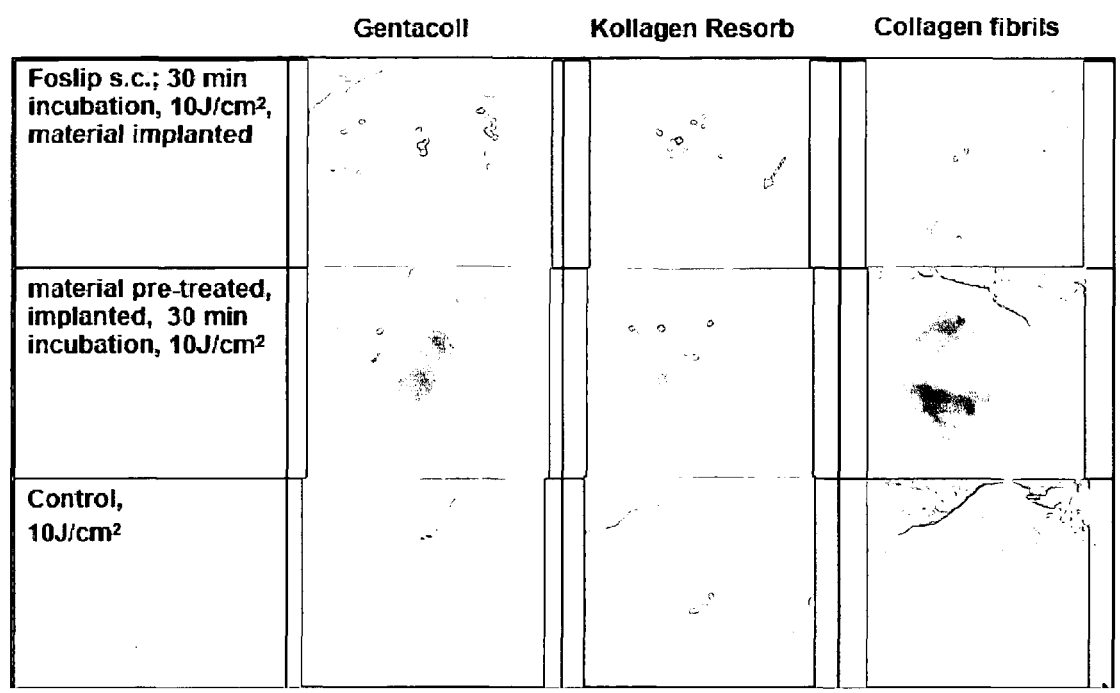
FIG. 3—shows biopsy results 14 days after treatment in mice.

Results from above animal study showed that collagen fibrils have best biocompatibility, In FIG. 3, photos show the biopsy results of the above treated mice after 14 days for the three groups with three different collagen products used. When the wound was pretreated with liposomal formulation of mTHPC, enhanced vascularization was observed.

EXAMPLE 3

Antimicrobial Effect of Collagen/mTHPC Mixture

Figure 4:
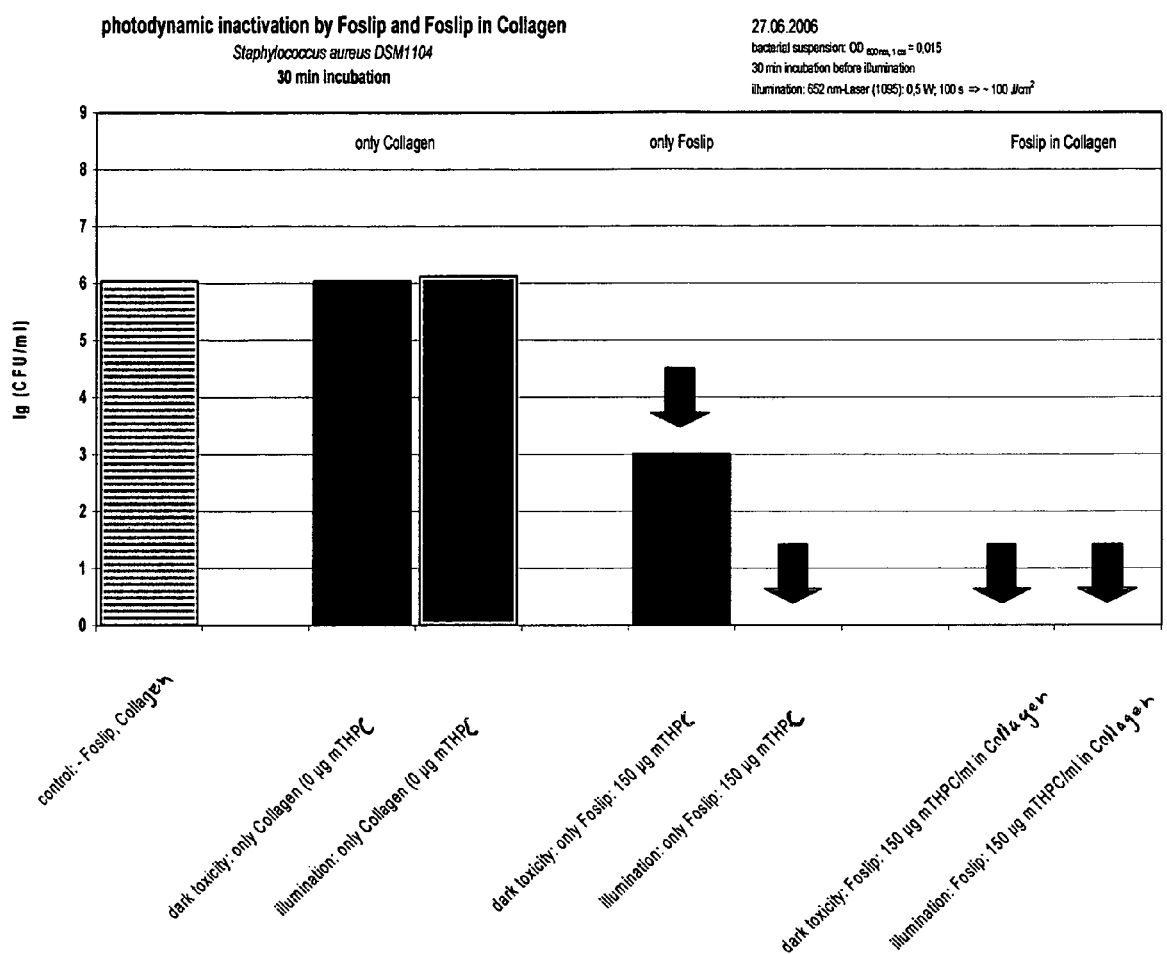
FIG. 4—depicts the antimicrobial effect of collagen/mTHPC mixture

Collagen and mTHPC was also tested on gram-positive bacteria *Staphylococcus aureus*. After 30 min incubation of bacteria with collagen alone with or without illumination no killing effect was noticed. When a liposomal formulation of mTHPC was used a slight dark toxicity effect and a strong killing effect on bacteria was noted when illuminated. The mixture of both, collagen and mTHPC formulation, led to a strong antimicrobial effect already without illumination. FIG. 4 illustrates the result of this study.

EXAMPLE 4

As Filler in Cosmetic Application

Figure 5:
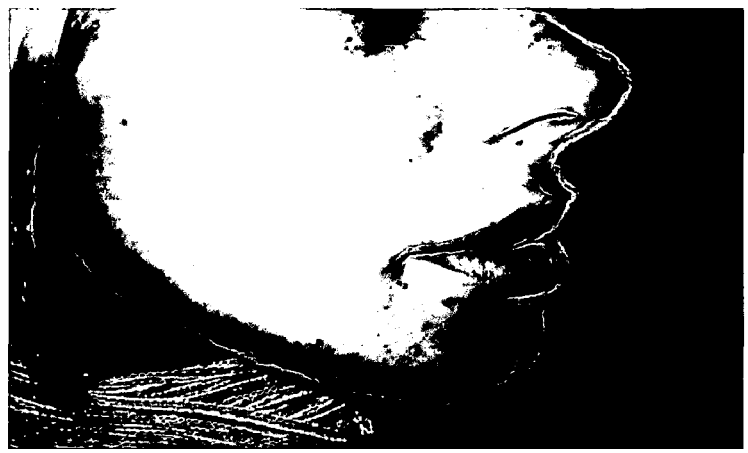
FIG. 5a—shows pictures before using the collagen and mTHPC filler product on lips.
FIG. 5b—show the lip picture after 9 month of using collagen and mTHPC filler product.
Figure 5:
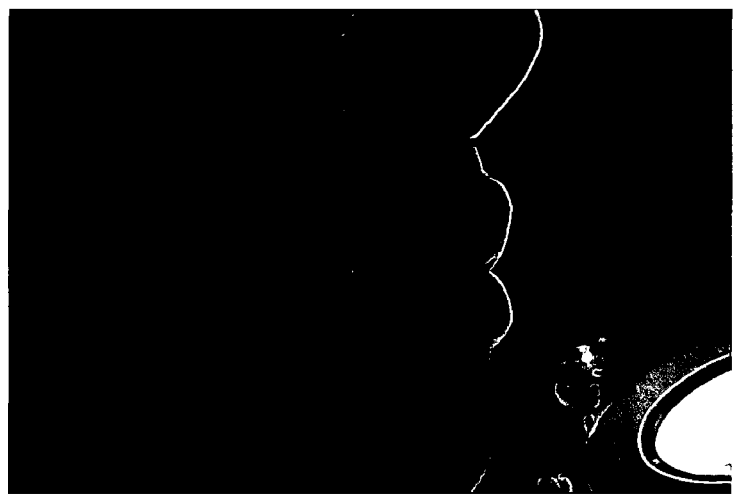

A mixture of a commercial collagen formulation (Zyplast) and a liposomal formulation of mTHPC was used as a dermal filler of lips. The mTHPC concentration was 0.05 mg/ml and the lip was irradiated by laser light at 652 nm. Due to the cross-linking of the collagen by mTHPC we could observe a longer lasting filling effect of the upper lip. Usually commercial collagen products will be resorbed within 4 to 6 month after injection. FIG. 5a shows the picture of before using filler and FIG. 5b shows the effect of the filler after 9 months.

EXAMPLE 5

Wound Closure and Healing Using Photochemical Product

Figure 6:
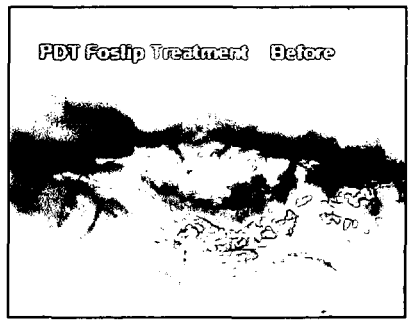
FIG. 6—before and after pictures of wound repair with present invention
Figure 6:
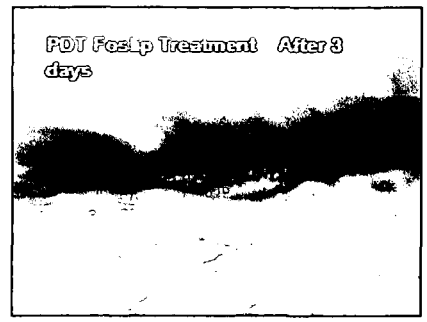

FIG. 6 shows the open wound before and after being treated with photochemical cross-linked collagen and irradiation. The open wound of the FIG. 6 is cleaned and disinfection before implanting the collagen matrix and liposome entrapped mTHPC mixture. After incubating for 1 hour the wound is irradiated with laser at 652 nm, and 20 J/cm$^2$. The laser irradiation helps in cross-linking the collagen fibrils and also disinfects the treatment area of microbial growth. The FIG. 6 shows the result of treatment after 3 days.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A method for in vivo cross-linking of structural proteins comprising the steps of:
    (a) formulating a mixture of a photosensitizer and said structural protein;
    (b) applying said mixture to tissue to be treated in a patient;
    (c) irradiating said treated tissue at a preselected wavelength;
    (d) photoactivating said photosensitizer; and
    (e) substantially simultaneously disinfecting the treatment site through photochemical reactions during photoactivation of said photosensitizer.

2. The method for in vivo cross-linking of structural proteins according to claim 1, wherein said irradiating step is by exposure to electromagnetic radiation having a wavelength between about 530 nm and 750 nm, in which the preselected wavelength overlaps sufficiently with the wavelengths of said photosensitizer's absorption spectrum to activate said photosensitizer.

3. The method for in vivo cross-linking of structural proteins according to claim 1, wherein said preselected wavelength is about 652 nm, said photosensitizer is temoporfin (mTHPC), and said structural protein is collagen.

* * * * *